United States Patent [19]

Sharaf

[11] Patent Number: 6,015,667
[45] Date of Patent: Jan. 18, 2000

[54] MULTICOMPONENT ANALYSIS METHOD INCLUDING THE DETERMINATION OF A STATISTICAL CONFIDENCE INTERVAL

[75] Inventor: Muhammad A. Sharaf, Oakland, Calif.

[73] Assignee: The Perkin-Emer Corporation, Foster City, Calif.

[21] Appl. No.: 08/659,115

[22] Filed: Jun. 3, 1996

[51] Int. Cl.[7] .............................. C12Q 1/68; C12P 19/34
[52] U.S. Cl. ............................................. 435/6; 435/91.2
[58] Field of Search ........................................ 435/6, 91.2

[56] References Cited

U.S. PATENT DOCUMENTS

| | | | |
|---|---|---|---|
| 4,962,037 | 10/1990 | Jett et al. | 435/6 |
| 5,614,386 | 3/1997 | Metzker et al. | 435/91.1 |

OTHER PUBLICATIONS

Prober et al, Science 238: 336–341, 1987.
Karger et al., Nucleic Acids Research 19 (18): 4955–4962 (1991), Mutiwave fluorescence detection for DNA sequencing using capillary electrophoresis.
Sweedler et al., Analytical Chemistry 63: 496–502 (1991); Fluorescence Detection in Capillary Zone Electrophoresis Using a Charge–Coupled Device with Time–Delayed Integration.
Thomas, Technometrics 33(4): 405–413 (1991), Errors–in–Variables Estimation in Multivariate Calibration.
Otto et al., Analytica Chimica Acta 180:455–456 (1986), Selectivity in Muticomponent Analysis.
Frans et al., Anal. Chem. 57:2680–2684 (1985), Selection of Analytical Wavelengths for Multicomponent Spectrophotometric Determinations.
Kalivas, Anal. Chem. 58: 989–992 (1986), Determination of Optimal Parameters for Multicomponent Analysis Using the Calibration Matrix Condition Number.
Thomas, Anal. Chemistry 66(15): 795A–804A (1994), A Primer on Multivariate Calibration.
Chanady et al., Beckman Instruments, Inc., Fullerton, California, Quantitative Analysis of Complex Mixtures with Multicomponent Analysis by Full Spectrum Quantitation (FSQ).
Haaland et al., Anal. Chem. 60: 1193–1202 (1988), Partial Least–Squares Methods for Spectral Analyses. 1. Relation to Other Quantitative Calibration Methods and the Extraction of Qualitative Information.
Salamin et al., "A wavelength and optical path length selection procedure for spectroscopic multicomponent analysis," *Chemometrics and Intelligent Laboratory Systems*, 11:57–62 (1991).
Connell et al., "Automated DNA Sequence Analysis," *BioTechniques* 5(4):342–348 (1987).

*Primary Examiner*—Eggerton A. Campbell
*Attorney, Agent, or Firm*—Paul D. Grossman

[57] ABSTRACT

A signal processing method in a processor is provided for performing a multicomponent analysis of a signal resulting from a spectral response of a mixture comprising a plurality of spectrally resolvable molecular species. The method provides both a determination of a concentration estimate and a statistical confidence interval for each species. In the method, a data vector d is received from a multichannel detector, data vector d having a length $n_c$, $n_c$ being the number of detector channels being monitored. A calibration matrix K having $n_c$ rows and $n_p$ columns is provided wherein $n_c$ is larger than $n_p$, $n_p$ being the number of spectrally resolvable molecular species. Next, a concentration estimate vector c having length $n_p$ is determined. Finally, a confidence interval $CI_i$ for each of the elements of the concentration estimate vector is determined according to the expression $$CI_i = c_i \pm (\text{varcovar}(c_{ii}))^{1/2} Q_{(cl,nf)}$$

where Q is the critical value of a statistical distribution for a given level of confidence, cl, and a given number of degrees of freedom $n_f$ where $n_f = n_c - n_p$. The invention further includes a program storage device embodying the method; a DNA sequencing process employing the method; and, an apparatus for carrying out the method.

13 Claims, 7 Drawing Sheets

MULTICOMPONENT ANALYSIS METHOD INCLUDING THE DETERMINATION OF A STATISTICAL CONFIDENCE INTERVAL

FIELD OF THE INVENTION

This invention relates to methods useful for the analysis of a signal resulting from the simultaneous measurement of the spectral response of a mixture containing a plurality of spectrally distinguishable species. In particular, the invention relates to a multicomponent analysis method using overdetermined measurements for the estimation the of relative concentration of each species including the determination of statistically valid confidence intervals for each such estimate.

REFERENCES

Caskey, C. T., U.S. Pat. No. 5,364,759 (1994)

Connell C. et al., *Biotechniques* 5: 342–348 (1987)

Draper, N. and Smith, H., "Applied Regression Analysis, 2nd Edition", John Wiley, New York (1981)

Frans, S. D. et al., *Anal. Chem.* 57: 2680–2684 (1985)

Hunkapiller, M. et al., U.S. Pat. No. 4,811,218 (1989)

Jolliffe, I. T., "Principle Component Analysis", p129–155, Springer-Verlag, New York (1986)

Kalivas, J. et al., *Anal Chem.* 58: 989–992 (1986)

Karger, A. et al., *Nucleic Acids Research* 19: 4955–4962 (1991)

Lee, L. G. et al., *Nucleic Acids Research* 20: 2471–2483 (1992)

Menchen, S. M. et al., U.S. Pat. No. 5,188,934 (1993)

Menchen, S. M. et al., U.S. Pat. No. 5,290,418 (1994)

Otto, M. et al., *Analytica Chimica Acta* 180: 445–456 (1986)

Sharaf, M. A., Anal. Chem. 58: 3084–3091 (1986)

Smith, L. M. et al., U.S. Pat. No. 5,171,534 (1992)

Thomas, E. V., *Anal. Chem.* 66: 795A–804A (1994)

Weber, J. L., U.S. Pat. No. 5,075,217 (1991)

BACKGROUND

Often it is desirable to perform an analysis of a sample containing multiple spectrally resolvable species wherein the relative concentrations of the component species are to be determined. Such simultaneous detection of multiple species in a single sample mixture has a number of advantages over serial analysis of multiple sample mixtures each containing only a single species. First, because only a single sample mixture is analyzed, fewer steps are required for sample processing and only a single measurement is required, both features resulting in a higher sample throughput and improved convenience to the user. Moreover, by combining multiple species into a single mixture, internal calibration is facilitated. An important example of a process utilizing such simultaneous multispecies spectral detection is multicolor DNA sequencing where four spectrally resolvable fluorescent dyes are simultaneously detected (Smith; Connell; Hunkapiller).

Because it is difficult to find a collection of reporters whose spectral response do not at least partially overlap, a problem common to all such simultaneous measurements is the determination of the concentration of each of the individual species given data that contains spectral contributions from multiple species. That is, to determine the individual species concentrations, the measured spectral data must be deconvolved. For example, FIG. 1 shows the emission spectra of four dyes used in four color DNA sequencing. It is clear from these spectra that it is impossible to identify a set of detection wavelengths that will result in both spectrally pure signal and sufficient emission intensity.

Linear multicomponent analysis is a powerful deconvolution method useful for the determination of the concentration of individual species given spectral data that contains contributions from multiple spectrally overlapping species (Frans; Kalivas; Thomas). In linear multicomponent analysis, a series of linear equations of the form $$d=Kc+r$$

are solved, where d is a vector whose elements correspond to a spectral response measured at a particular wavelength, K is a calibration matrix whose elements correspond to pure component linear response constants for each species at each channel, c is a concentration estimate vector whose elements correspond to an estimate of the concentration of a particular species in a mixture, and r is a residual vector of the concentration estimate vector c. (Note that throughout this disclosure, matrices are designated by boldface capital letters and vectors are designated by boldface lowercase letters.) Thus, given measured values d and calibration matrix K, estimated values for the individual concentration of each species c can be determined. The above equation is written in a form which assumes that vectors d and r are column vectors. If vectors d and r are expressed as row vectors, the preceding equation becomes, $$d=K^T c^T + r$$

Throughout this disclosure, it will be assumed that vectors d and r column vectors.

In addition to obtaining an estimated value for the concentration of each species in a mixture, it is desirable to obtain a quantitative figure of merit for the quality of the estimate. For example, in the case of multicolor DNA sequencing methods, it is useful to have a measure of the quality of a particular base call in a sequence. This is particularly true for the case of sequences including heterozygote positions where two bases may be present at a given position in the sequence. The most common such figure of merit used in linear multicomponent analysis is the condition number of the calibration matrix, cond(K), where $$\mathrm{cond}(K)=\|K\|\cdot\|K^{-1}\|$$

where the double brackets indicate the norm of the matrix (Otto).

However, the condition number is not an optimal figure of merit for indicating the quality of a multicomponent concentration estimate. The condition number is a measure of the quality of a calibration matrix K rather than a measure of the quality of a particular multicomponent measurement. Thus, it is possible for a system to have a favorable condition number, but, because of certain experimental factors, result in a particularly uncertain measurement. For example, the condition number provides no guidance as to how a noisy signal impacts the quality of a particular multicomponent concentration estimate.

Thus, there is a need for a statistically meaningful figure of merit for determining the quality of a concentration estimate based on the spectral response of a mixture containing a plurality of spectrally distinguishable species using multicomponent analysis methods.

SUMMARY

The present invention is directed towards the discovery of a signal processing method in a processor comprising a multicomponent analysis process employing overdetermined measurements for the estimation of the relative concentration of each of a plurality of spectrally resolvable species present in a mixture, including the determination of a valid figure of merit for evaluating the quality of the estimate.

In a first aspect, the invention includes a signal processing method in a processor for performing a multicomponent analysis of a signal resulting from a spectral response of a mixture containing a plurality of spectrally resolvable molecular species. The method provides for the determination of a concentration estimate and a statistical confidence interval for each species in the mixture. The method includes the following steps. First, a data vector d is received from a multichannel detector, where data vector d has a length $n_c$, $n_c$ being the number of detector channels being monitored. A calibration matrix K is provided, where K has $n_c$ rows and $n_p$ columns, $n_p$ being the number of spectrally resolvable molecular species. In an important feature of the invention, $n_c$ is larger than $n_p$, making K a non-square matrix. Next, a concentration estimate vector c is determined, where c has length $n_p$. Finally, a confidence interval $CI_i$ is determined for each of the elements of the concentration estimate vector according to the expression $$CI_i = c_i \pm (\text{varcovar}(c_{ii}))^{1/2} Q_{(cl,nf)}$$

where Q is the critical value of a statistical distribution for a given level of confidence, cl, and a given number of degrees of freedom $n_f$, where $n_f = n_c - n_p$.

In one preferred embodiment of the invention, $n_c$ is greater than 10, and more preferably $n_c$ is greater than 20.

In a second preferred embodiment of the method of the invention, the ratio $n_c/n_p$ is chosen to be greater than 1.5. More preferably the ratio is greater than 3. More preferably still, the ratio is chosen to be greater than 5.

Preferably, the statistical distribution used in the method is the Student's t distribution or the Gaussian distribution.

In another preferred embodiment for processing multiple temporally related data vectors, the method is repeated at regular intervals for a defined period.

The step of determining a concentration estimate vector is preferably effected using the expression $$c = (K^T K)^{-1} K^T d.$$

The step of determining of a confidence interval preferably includes the steps of: determining a residual vector r of the concentration estimate vector c where $$r = d - Kc$$

determining a variance of the data vector d, var(d), where $$\text{var}(d) = \frac{r^T r}{(n_c - n_p)},$$

and, determining a variance-covariance matrix of the concentration estimate vector c, varcovar(c), where $$\text{varcovar}(c) = \text{var}(d) \, (K^T K)^{-1}.$$

In a second aspect, the invention includes a program storage device readable by a machine, tangibly embodying a program of instructions executable by a machine to perform the method steps of the multicomponent analysis method described above.

In a third aspect, the invention includes a method of polynucleotide sequencing. In the method a mixture is formed comprising a first, a second, a third, and a forth class of labeled polynucleotides such that each polynucleotide in the first class includes a 3'-terminal dideoxyadenosine and is labeled with a first label each polynucleotide in the second class includes a 3'-terminal dideoxycytidine and is labeled with a second label, each polynucleotide in the third class includes a 3'-terminal dideoxyguanosine and is labeled with a third label and each polynucleotide in the forth class includes a 3'-terminal dideoxythymidine and is labeled with a forth label. The labels are chosen such that each of the first, second, third, and fourth labels may be spectrally resolved. The labeled polynucleotides are electrophoretically separated thereby forming bands of similarly sized polynucleotides. Each of the bands are detected using a spectral array detector having $n_c$ channels, where $n_c$ is greater than four. The signal from the spectral array detector is processed according to the method of the invention and values of $c_i$ and $CI_i$ are reported for a series of time values.

In a fourth aspect, the invention includes an apparatus for measuring the spectral response of a sample including a mixture containing $n_p$ spectrally distinguishable species. A spectral array detector is provided for detecting the spectral response of the sample, the detector having $n_c$ channels where $n_c$ is greater than $n_p$, the output of the detector being a signal representing a light intensity at a particular channel at a particular time. A signal processor is provided for receiving the signal from the spectral array detector, the signal processor being configured to perform the method steps of the signal processing method of the invention.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Figure 1:
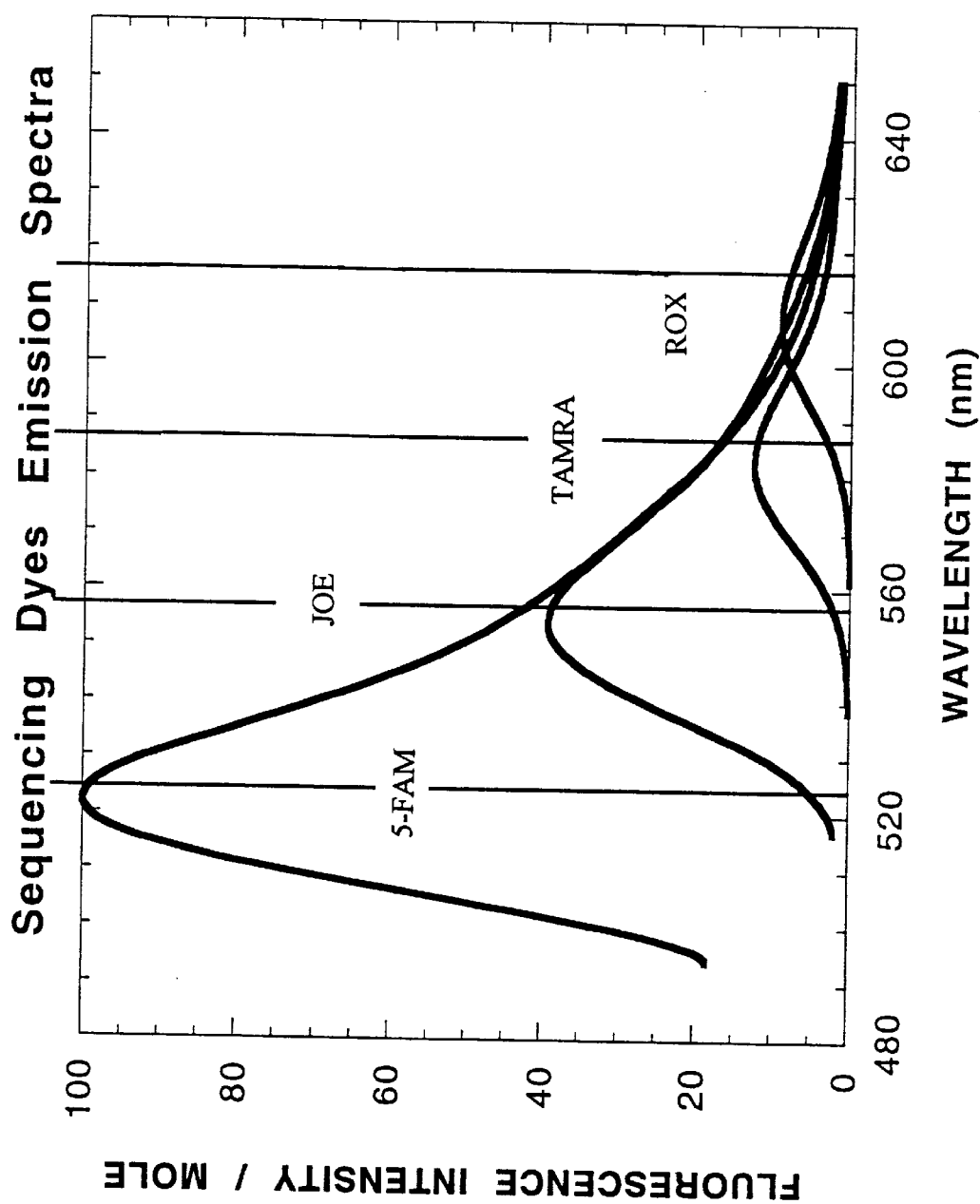
FIG. 1 shows emission spectra for a dye set used in four color DNA sequencing methods.
Figure 2:
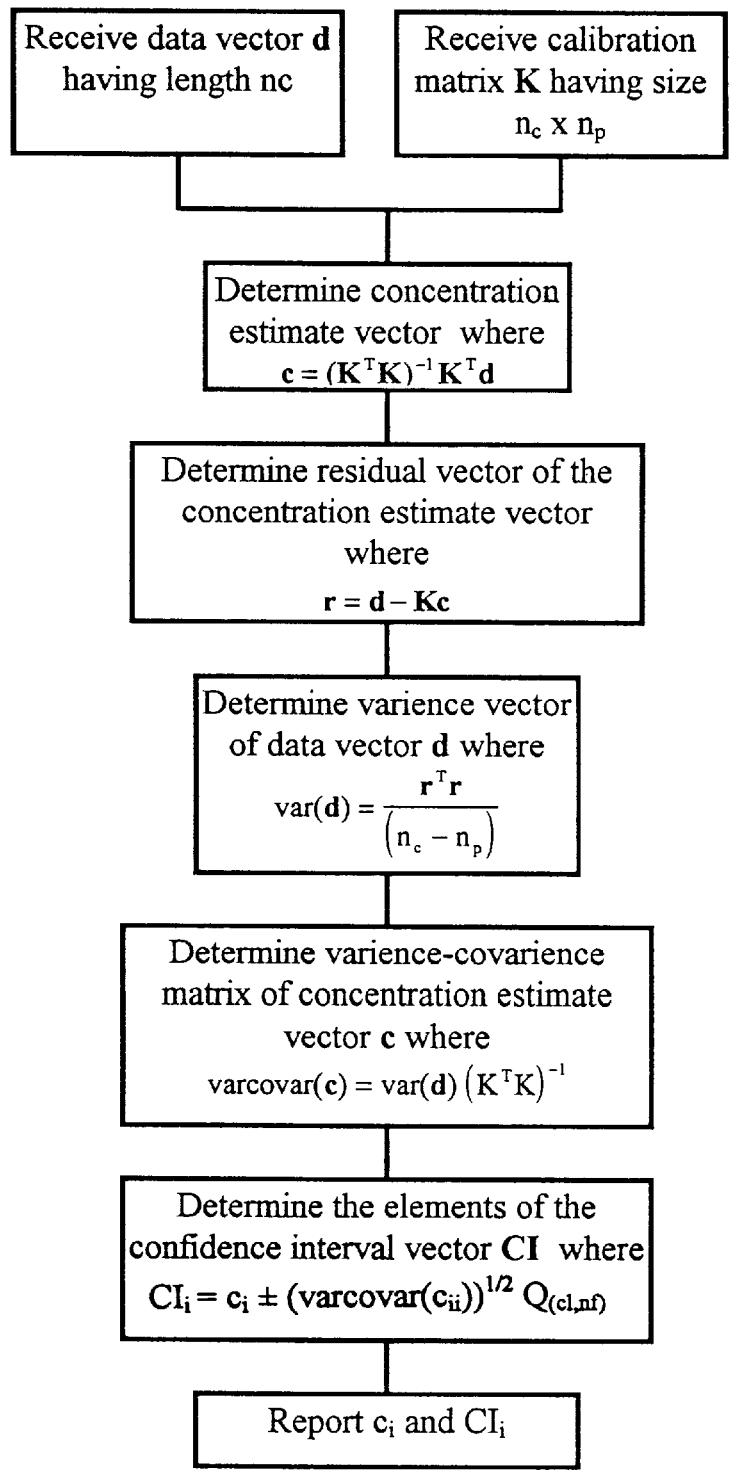
FIG. 2 is a flow chart generally describing a preferred embodiment of the multicomponent analysis method of the invention.

The present invention is directed generally to a signal processing method in a processor for performing multicomponent analysis, such method employing the use of overdetermined measurements for the estimation of the relative concentration of each of a plurality of spectrally resolvable species present in a mixture and the determination of a statistically valid confidence interval for each such concentration estimate. Generally, the method of the invention comprises the steps of (i) receiving a data vector d from a multichannel detector; (ii) providing a calibration matrix K having $n_c$ rows and $n_p$ columns wherein $n_c$ is larger than $n_p$, $n_c$ being the number of detector channels being monitored, and $n_p$ being the number of spectrally resolvable molecular species; (iii) determining a concentration estimate vector c having length $n_p$, the magnitude of each matrix element $c_i$, representing a concentration estimate of a particular species i; and (iv) determining a confidence interval for each of the elements of the concentration estimate vector $CI_i$ according to the expression $$CI_i = c_i \pm (\text{varcovar}(c_{ii}))^{1/2} Q_{(cl,nf)}$$

where Q is the critical value of a statistical distribution for a given level of confidence, cl, and a given number of degrees of freedom $n_f$ where $n_f = n_c - n_p$. FIG. 2 shows a flow diagram of one preferred embodiment of the multicomponent analysis method of the invention.

I. DEFINITIONS

Unless stated otherwise, the following terms and phrases as used herein are intended to have the following meanings.

The "spectral response" of a sample refers to the degree to which a sample absorbs, scatters, and/or emits radiation including the wavelength and/or magnitude of such absorption, scatter, and/or emission. Examples of process capable of providing a spectral response include UV-Visible absorbance, chemiluminescense, fluorescence, electrochemiluminescense, Ramman spectroscopy, and the like.

As used herein, the term "confidence interval" refers to a range of values which will include the true average value of a parameter a specified percentage of the time. Thus, if the average purity of a sample is 99.95%±0.25% at the 95% confidence level, 95% of the time the estimated purity estimated in the same way will be in the range of 99.95%±0.25%.

The term "multichannel detector" refers to a detector comprising an array of independently addressable detector elements sensitive to electromagnetic radiation, such as a diode array, a charged coupled device (CCD) system, an array of photomultiplier tubes, or the like.

II. MULTICOMPONENT ANALYSIS METHOD

A. The Signal

The signal processor of the invention receives a signal generated by a multichannel spectral array detector which monitors the spectral response of a mixture containing a plurality of spectrally distinguishable molecular species. The magnitude of the output of the spectral array detector is proportional to light intensity. The channel location of the measurement is related to the wavelength of the measured light either directly, or through the use of a spectral separation means. One example of such a spectral array detector is provided by Karger et al. (Karger).

B. The Data Vector

Data vector d is a vector having a length $n_c$, where $n_c$ corresponds to the number of detector channels being monitored by a multichannel detector. The magnitude of each vector element $d_i$ represents a signal intensity at a particular detector channel at a given time. In an important feature of the invention, the number of detector channels being monitored, $n_c$, is greater than the number of spectrally resolvable species being detected, $n_p$. Preferably, $n_c/n_p$ is greater than 1.5; more preferably, $n_c/n_p$ is greater than 3; most preferably, $n_c/n_p$ is greater than 5. This "over sampling" of the spectral response is necessary in order to construct an overdetermined linear system for the purpose of allowing the calculation of a residual vector of a concentration estimate vector. If $n_c = n_p$, the system represents an exactly determined system for which no residuals can be estimated.

C. The Calibration Matrix

Calibration matrix K is a $n_c \times n_p$ nonsquare matrix of pure-component linear response constants representing the individual contribution of each of the $n_p$ species to the signal detected at each of the $n_c$ detector channels. Values of the elements of the calibration matrix, $K_{ij}$, are determined by measuring the pure-component response for each species for each detector element. Preferably, the values of the elements of K are normalized such that the sum of the normalized values for all channels is unity. Such normalization facilitates the quantitative comparison of results between different channels and different scans.

D. The Concentration Estimate Vector

The concentration estimate vector represents an estimate of the concentration of each individual species in a mixture containing multiple spectrally resolvable species based on a spectral response which includes contributions from multiple spatially overlapping species. Given a data vector d and a calibration matrix K, in one preferred embodiment, c is ascertained by evaluating the expression, $$c = (K^T K)^{-1} K^T d$$

where the superscript "T" indicates the transpose of the matrix K. The concentration estimate vector c is a vector of length $n_p$, where as before, $n_p$ is the number of spectrally resolvable species whose concentration is to be estimated. Thus, values of the elements of the concentration estimate vector, $c_i$, represent estimates of the concentration of each of the $n_p$ species.

In the present discussion and examples, the concentration estimate vector c and the residual vector r are estimated using the method of unweighted least squares multiple regression Draper). Other regression methods may also be used in the method of the invention, including but not limited to, weighted least squares regression (Draper), principle component regression (Jolliffe), latent root/ridge regression techniques (Draper), as well as relationships based on scores obtained from principle components and/or factor analysis (Sharaf). In each case, the concentration estimate provides an estimate of r, which is subsequently used to estimate the measurements variance and the confidence intervals for $c_i$'s. Weighted least squares regression is typically used when some measurements (channels) have higher variance than others. In such cases a weighting matrix is used to account for the unequal variances. The weighting matrix is subsequently used to estimate the variance in c and the confidence intervals of $c_i$'s (Draper p 108–116). Principal component regression is used when the parent spectra are highly correlated. In this approach the relationship between d, K and c is expressed in the factor/principal components score space (Jolliffe; Sharaf) The regression estimates obtained the score spaces are then transformed to c using the eigenvectors (Jolliffe).

E. Determination of Confidence Intervals for Each Concentration Estimate

Given data vector d containing measured values of the spectral response of a sample at each detector element, calibration matrix K representing the individual pure-component response of each species at each detector element, and concentration estimate vector c representing an estimated concentration of each of the component species, a confidence interval associated with each concentration estimate is determined, $CI_i$.

The first step in calculating a confidence interval $CI_i$ for each concentration estimate $c_i$ according to the present invention is to calculate a residual vector r associated with the concentration estimate vector c. Generally, a residual vector is a vector representing the difference between a vector representing observed values of a parameter and a vector representing estimated values of that parameter calculated from a regression equation. Thus, in the present method, the residual vector is the difference between the observed data vector d and the estimated vector Kc, such that $$r = d - Kc$$

Next, based on the value of residual vector r evaluated above, a variance is calculated for the data vector, var(d), where var(d) is a measure of the instrumental and environmental uncertainties associated with a particular measurement, e.g., stray light reaching the detector, electronic noise in the circuitry of the detector, and other like uncontrolled experimental factors. Var(d) is given by the following expression, $$\text{var}(d) = \frac{r^T r}{(n_c - n_p)}$$

where $n_c$ and $n_p$ are as defined above. Note that for methods utilizing a square calibration matrix, i.e., where $n_c = n_p$, no residuals can be determined because the ratio in the above expression is undefined. Such exactly determined linear systems provide no "statistically valid" measure of the quality of the estimated parameter.

Next, a variance-covariance matrix of the concentration estimate vector c is determined, varcovar(c), where varcovar (c) is a measure of how the above mentioned measurement errors are reflected in the concentration estimate vector c. Varcovar(c) is evaluated using the following expression, $$\text{varcovar}(c) = \text{var}(d) \, (K^T K)^{-1}$$

Finally, a specified confidence interval for each element $c_i$ of the concentration estimate vector c is evaluated, $CI_i$, where $$CI_i = c_i \pm (\text{varcovar}(c_{ii}))^{1/2} Q_{(cl, n_f)}$$

where Q is a critical value of a statistical distribution for a given level of confidence, cl, and a given number of degrees of freedom, $n_f$, where in the present case, $n_f = (n_c - n_p)$, and varcovar($c_{ii}$) refers to the $i^{th}$ diagonal element of the varcovar(c) matrix. As used herein, the term "critical value" refers to a value of a statistical distribution for which the integrated area under the distribution curve for values greater than the critical value is equal to (1-confidence level). Exemplary statistical distributions include the normal or Gaussian distribution, the Poisson distribution, the $\chi^2$ distribution, the F distribution, the Student's t distribution, and the binomial distribution. The particular distribution chosen to will depend on the specific application. Preferably, a Gaussian or Student's t distribution is used. More preferably, when $n_f < 30$ the Student's t distribution is used, and when $n_f > 30$ the Gaussian distribution is used. For example, to determine the 99% confidence interval for a system having 16 degrees of freedom using the Student's t distribution, the value of Q is 2.92.

III. APPARATUS

Figure 6:
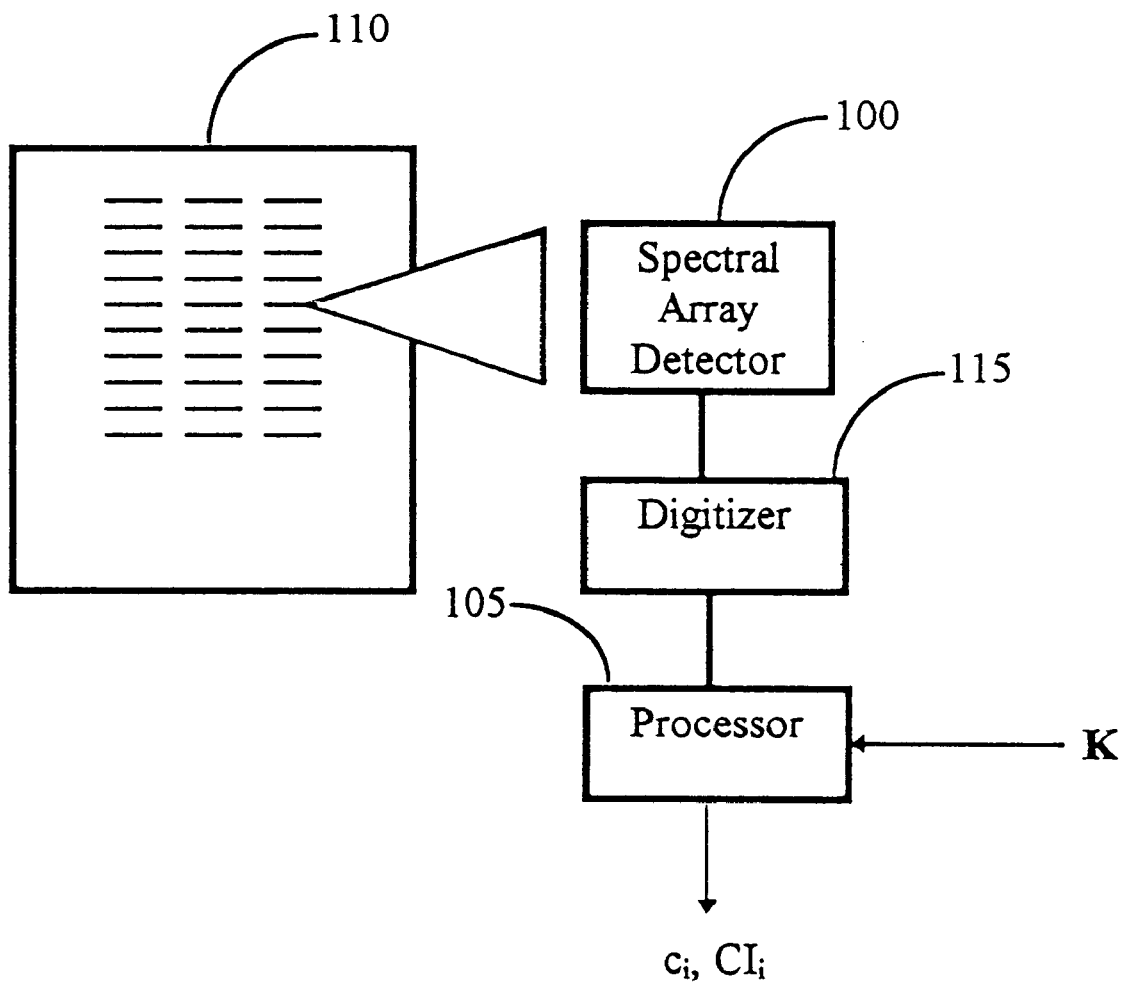
FIG. 6 shows an apparatus useful for the measurement and analysis of a spectral response of a mixture containing a plurality of spectrally distinguishable molecular species according to the methods of the invention.

In one aspect, the present invention includes an apparatus useful for the measurement and analysis of a spectral response of a mixture containing a plurality of spectrally distinguishable molecular species. Referring to FIG. 6, the apparatus of the invention includes (i) a spectral array detector 100 including multiple detection channels, such channels being related to the wavelength of light encountering each channel; (ii) a signal processor 105 for performing the multicomponent analysis process of the invention on the signal produced by the spectral array detector; and, optionally, (iii) a separation means 110 for partially spatially separating the plurality of spectrally distinguishable species. In a preferred configuration, the apparatus includes a digitizer 115 for digitizing the signal from the spectral array detector prior to transmission to the processor.

A. The Spectral Array Detector

As used herein, the term "spectral array detector" refers to a detector which employs (i) a means to spectrally separate light forming a spectral response from a sample, such as a diffraction grating, a prism, a beam splitter in combination with optical filters, or the like; (Ii) a multichannel detector; (iii) optionally a light source, such as an incandescent bulb, an arc lamp, a laser, a laser diode, or the like; and (iv) associated optics capable of directing and conditioning the light from the light source and/or the light used to define the spectral response of the sample.

Figure 3:
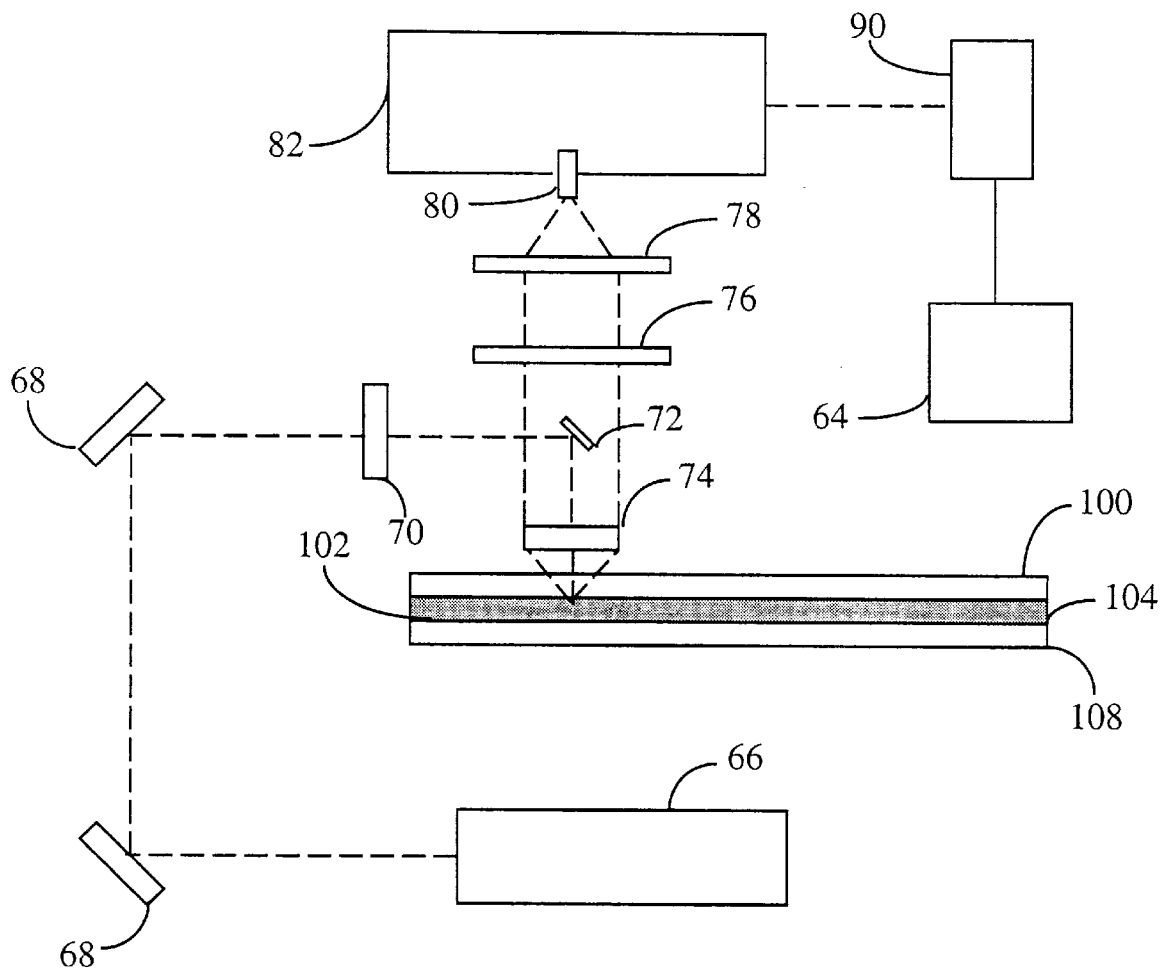
FIG. 3 shows a preferred light path for a spectral array detection system useful for the measurement of the spectral response of a mixture containing a plurality of spectrally distinguishable fluorescent species.

FIG. 3 shows a schematic diagram of the light path of a preferred embodiment of a spectral-array detection system useful in a real time fluorescence-based multicolor electrophoresis scanner. The detection system uses a laser as a fluorescence excitation light source, e.g. an argon ion laser that emits a 40 mW, 0.67 mm diameter polarized light beam having intensity maxima at wavelengths of 488 and 514 nm. Light from laser (66) is reflected off of adjustably-mounted turning mirrors (68) which direct the laser light to a desired location. Telescope lenses (70) then reduce the beam diameter to approximately 100 μm, and bending mirror (72) directs the light into electrophoresis medium (104) at right angles. Light emitted from the laser-excited fluorescent label is collected by aspheric collection lens (74) which collimates the light in the direction of the detector. The emitted light then passes around bending mirror (72) and through laser rejection filter (76), thereby reducing the level of scattered laser light entering the detector. Because the excitation laser light passes through the center of aspheric collection lens (74), a certain amount of laser light will be reflected directly back from the lens surface in the direction of the detector, causing unwanted background signal. Bending mirror (72), which is mounted in the center of laser rejection filter (76), acts to deflect this reflected light away from the collection path thus reducing the amount of reflected light entering the detector. The collected emission light then passes through plano-convex lens (78) which focuses the emission light at slit (80) mounted on the entrance to spectrograph (82). (Spectrograph (82) utilizes a 405 g/mm, 450 nm blaze grating with a dispersion of 17 nm/mm.) After passing through spectrograph (82), the light then falls onto CCD (90). Because the spectral separation of the emission light is rarely complete, the light falling on each detector channel will be a combination of emissions from multiple species. The output signal from CCD (90) is transmitted to signal processor (64) for subsequent multicomponent analysis and data presentation. In order to interrogate multiple electrophoresis lanes on a real-time basis, the optical system described above, less turning mirrors (68) and computer (90), may be scanned across the width of the electrophoresis chamber.

B. The Signal Processor

In a preferred embodiment of the present invention, the steps of above-described multicomponent analysis method are performed by a signal processor 105 specially configured to carry out the steps of the multicomponent analysis method of the invention. Such a signal processor can take the form of a generic microprocessor driven by appropriate software, a dedicated microprocessor using embedded firmware, or a customized digital signal processing circuit (DSP) which is dedicated to the specific data acquisition, analog-to-digital conversion, matrix manipulation, or filtering operation required by the method.

In one preferred embodiment, the signal processor comprises (i) a memory for storing a digitized representation of the signal and calibration matrix, and (Ii) a processor for carrying out the various steps of the method. In such a case, the above method steps are embodied in a program storage device readable by a machine, such program storage device including a computer readable medium. Computer readable media include magnetic diskettes, magnetic tapes, optical disks, Read Only Memory, Direct Access Storage Devices, and any other like medium.

C. Separation Means

In a preferred embodiment of the invention, the spectrally distinguishable species are detected subsequent to being partially spatially separated by a separation process, e.g., chromatography, electrophoresis, and the like. In a particularly preferred embodiment, the species are partially resolved by electrophoresis prior to detection. Preferably the type of electrophoretic matrix is crosslinked or uncrosslinked polyacrylamide having a concentration (weight to volume) of between about 2–20 weight percent. More preferably, the polyacrylamide concentration is between about 4–8 percent. Preferably in the context of DNA sequencing in particular, the electrophoresis matrix includes a strand separating, or denaturing, agent, e.g., urea, formamide, and the like. Detailed procedures for constructing such matrices are given in *ABI PRISM™ 377 DNA Sequencer User's Manual, Rev. A,* January 1995, Chapter 2 (p/n 903433, The Perkin-Elmer Corporation, Foster City, Calif. (PE)). The optimal polymer concentration, pH, temperature, concentration of denaturing agent, etc. employed in a particular separation depends on many factors, including the size range of the molecular species to be separated, their compositions, whether, if nucleic acid, they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20–300 bases have been separated and detected in accordance with the invention in the following matrix: 6 percent polyacrylamide made from 19 parts to 1 part acrylamide to bis-acrylamide, formed in a Tris borate EDTA buffer at pH 8.3.

Alternative electrophoretic sieving matrices include micellar networks formed from the class of copolymers composed of hydrophilic polymer segments having uniform segment lengths a plurality of hydrophobic polymer segments carried on and spaced from one another, at regular repeating intervals, by the hydrophillic polymer segments, e.g., $(C_6F_{13})_2PEG35000$, $(C_8F_{17})_2PEG35000$), and the like (Menchen 1994).

IV. BIOANALYTICAL APPLICATIONS

The methods of the present invention are well suited to any method requiring the simultaneous detection of multiple spatially-overlapping spectrally resolvable analytes. However, the methods of the invention are particularly well suited for identifying spectrally resolvable classes of polynucleotides that have been subjected to a biochemical separation procedure, such as electrophoresis or chromatography, where a series of bands or spots of target substances having similar physiochemical properties, e.g., size, conformation, charge, hydrophobicity, or the like, are present in a linear or planar arrangement. As used herein, the term "bands" includes any spatial grouping or aggregation of analytes on the basis of similar or identical physiochemical properties, e.g., in the separation of dye-polynucleotide conjugates by electrophoresis.

Classes of polynucleotides can arise in a variety of contexts. In a preferred category of methods referred to herein as "fragment analysis" methods, labeled polynucleotide fragments are generated through template-directed enzymatic synthesis using labeled primers or nucleotides, e.g., by ligation or polymerase-directed primer extension The fragments are subjected to a size-dependent separation process, e.g., electrophoresis or chromatography, where multiple classes of polynucleotides are separated simultaneously and the different classes are distinguished by spectrally resolvable labels. The separated fragments are then detected subsequent to the separation, e.g., by laser-induced fluorescence.

One such fragment analysis method is based on variable number of tandem repeats, or VNTRs (Weber, Caskey). VNTRs are regions of double-stranded DNA that contain adjacent multiple copies of a particular sequence, with the number of repeating units being variable. Many of these repeat regions are abundant, highly polymorphic, and uniformly distributed throughout the human genome, and can therefore serve as useful genetic markers. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n—(dG-dT)n dinucleotide repeat family (also called the (CA)n dinucleotide repeat family). There are thought to be as many as 50,000 to 100,000 (CA)n repeat regions in the human genome, typically with 15–30 repeats per block Preferably, in VNTR or SIR methods, label is introduced into the polynucleotide fragments by using a dye-labeled PCR primer. In a preferred method for carrying out VNTR methods, multiple loci are separated in a single electrophoresis lane and fragments from each loci are labeled with a different spectrally resolvable label. By running multiple loci in a single lane, sample throughput is greatly increased and a differentially labeled internal lane standard may be employed.

In a particularly preferred DNA sequencing method, classes identified in accordance with the invention are defined in terms of terminal nucleotides such that a correspondence is established between the four possible terminal bases and the members of a set of spectrally resolvable dyes (Smith). Such sets of spectrally resolvable dyes useful for DNA sequencing are well known in the art of DNA sequencing (Smith; Menchen 1993; Lee). More preferably, the classes arise in the context of the chemical or chain termination methods of DNA sequencing, and most preferably the classes arise in the context of the chain termination method, i.e., dideoxy DNA sequencing, or Sanger sequencing. This method involves the synthesis of a DNA strand by a DNA polymerase in vitro using a single-stranded or double-stranded DNA template whose sequence is to be determined. Synthesis is initiated at only the one site where an oligonucleotide primer anneals to the template. The synthesis reaction is terminated by incorporation of a nucleotide analog that will not support continued DNA elongation. The chain-terminating nucleotide analogs are the 2',3'-dideoxynucleoside 5'-triphosphates (ddNTPs) which lack the 3'—OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP can be incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides. As in the case of VNTR analysis, it is particularly preferred to run more than a single class of labeled polynucleotides in a single lane because sample throughput is greatly increased and ambiguities due to lane-to-lane variability in electrophoretic mobility are eliminated.

V. EXAMPLES

The invention will be further clarified by a consideration of the following examples, which are intended to be purely exemplary of the invention and not to in any way limit its scope.

EXPERIMENTAL

The data used in the following examples were collected using an ABI Model 310 Genetic Analyzer (The Perkin-Elmer Corporation, p/n 310-00-100/120). The Model 310 is a capillary electrophoresis based system employing multi-color fluorescence detection. The detector includes a diffraction grating for spectrally separating fluorescence emission light and a CCD multichannel detector to measure the intensity of the spectrally separated light as a function of wavelength. The CCD detector used to collect the data was operated such that from four to twenty different collection channels were sampled corresponding to a wavelength range from 525 nm to 663 nm. In each case, each channel had a wavelength range of 7 nm. The separation medium used in the examples was a 5% fluorocarbon-based micellar polymer matrix [2.5% $(C_6F_{13})_2PEG35000+2.5\%$ $(C_{-8},F_{17})_2PEG35000)$] formulated with 6.6 M urea, 0.66 M pyrrolidinone, 100 mM TAPS buffer (adjusted to pH 8.0 with NaO) (Menchen 1994). The capillary electrophoresis capillary was 47 cm long with an internal diameter of 75 $\mu$m and internally coated with fluorohydrocarbon (DB-210 coating from J&W Scientific). The separation distance from the injection end of the capillary to the detector window was 36 cm. A heating plate for controlling the temperature of the capillary was set at 42° C. An electrophoresis running voltage of 160 v/cm was used. The electrolyte reservoirs each contained 100 mM TAPS buffer (pH 8.0). Samples were resuspended in 25 $\mu$l of Template Suppression Reagent (PE p/n 401674).

EXAMPLE 1

Generating a Calibration Matrix

The following example describes the preparation of a calibration matrix K to be used in the multicomponent analysis method of the invention in the context of a 4-color DNA sequencing experiment.

Applied Biosystems Taq DyeDeoxy® Terminator Standards were used to prepare the calibration matrix according to enclosed instructions (PE p/n 401071). Each standard mixture consisted of fragments resulting from a Sanger-type DNA sequencing extension reaction, the fragments of each of the mixtures terminating in a different base, A, B, C, or T. The fragments of each standard mixture were labeled with a different spectrally resolvable fluorescent dye: the A-terminated fragments with rhodamine 6; G (R6G), the G terminated fragments with rhodamine 110 (R110), the C terminated fragments with rhodamine X (ROX), and the T terminated fragments with tetramethyl rhodamine (TAMRA). Each of the standard mixtures was run separately on the Model 310 system under conditions described above. The matrix standards were injected onto the capillary or 30 s at 40 V/cm.

Figure 4:
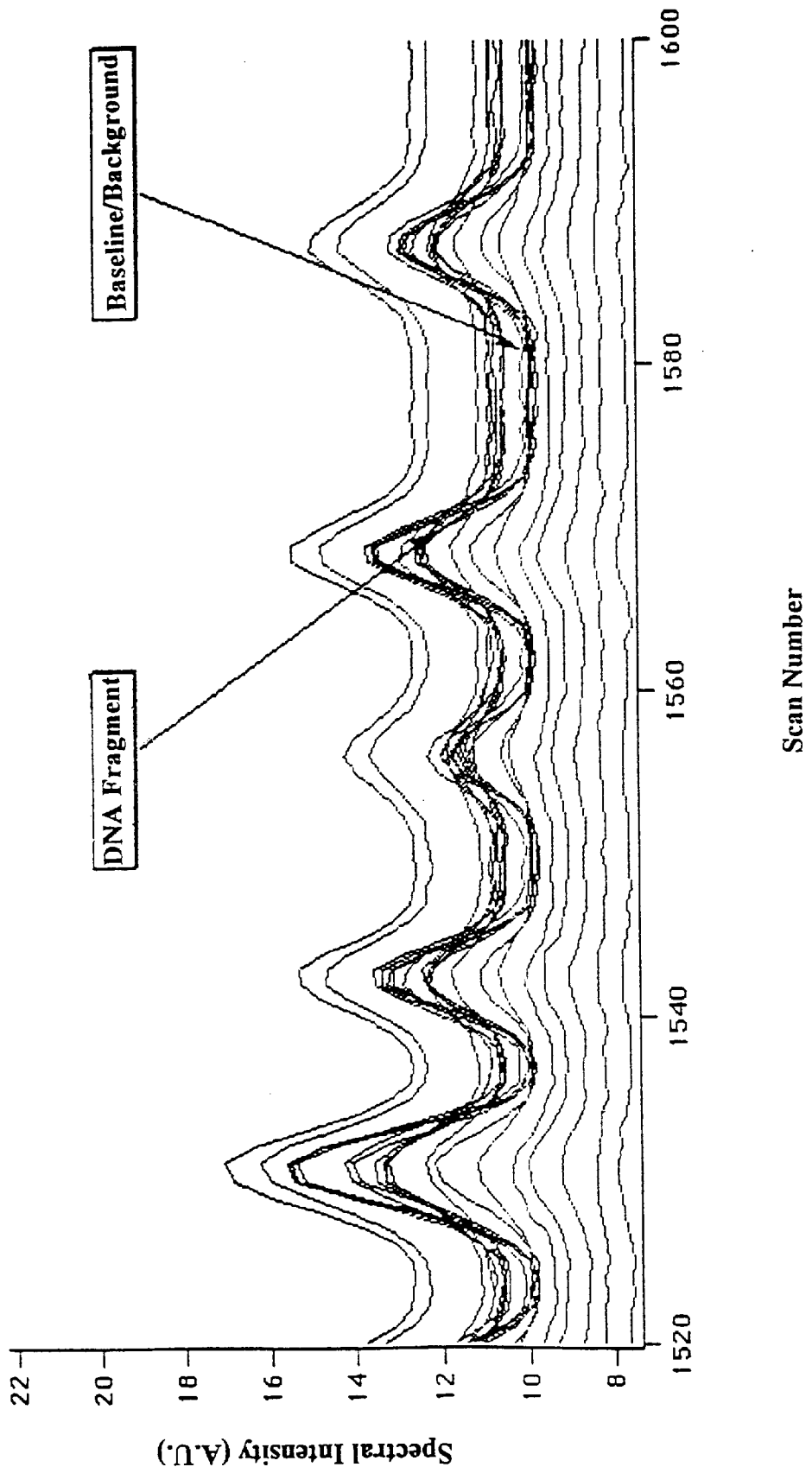
FIG. 4 shows a 20-channel electropherogram of an A-terminated standard calibration mixture labeled with the dye R6G.

FIG. 4 shows a segment of data showing the A-terminated standard mixture labeled with R6G. The figure shows data collected from channel 1 through 20 from scan number 1520 to scan number 1600, where each scan number corresponds to approximately 1 s. Data from each of channels 1 through 20 are shown in the figure.

To obtain baseline-corrected normalized data for the calibration matrix, the following procedure was used. First, a scan number was identified corresponding to a local signal maximum, e.g., in this case scan number 1570. Next, a scan number was identified corresponding to an unperturbed baseline value, e.g., in this case scan number 1581. Then, data was collected from each of the 20 detector channels at each of the two selected scan numbers. Next, to baseline correct the signal maximum data, a corrected scan value was computed by subtracting the baseline data from the signal maximum data. Finally, the corrected scan data was normalized such that the sum of the corrected scan data from all 20 channels was unity, e.g., in this case, each corrected scan value was divided by 36,142. The above procedure may be repeated for other peak/baseline data pairs in order to obtain a more robust estimate of the calibration spectra for each standard mixture. The normalized corrected scan values were used to form the calibration matrix Table 1 below shows the signal maximum data (scan 1570), the baseline data (scan 1581), corrected scan data, and normalized corrected scan data for each of channels 1–20.

Table 1

Maximum Data, Baseline Data, Corrected Data, and Normalized Corrected Data Collected at 20 Channels Based on Scans 1570 and 1581

TABLE 1

Signal Maximum Data, Baseline Data, Corrected Data, and Normalized Corrected Data Collected at 20 Channels Based on Scans 1570 and 1581

| Channel Number | Scan 1570 | Scan 1581 | Corrected Scan | Normalized Corrected Scan |
|---|---|---|---|---|
| 1 | 8369 | 8178 | 191 | 0.00528471 |
| 2 | 9693 | 9046 | 647 | 0.01790161 |
| 3 | 11254 | 9744 | 1510 | 0.041779647 |
| 4 | 12554 | 9898 | 2656 | 0.073487909 |
| 5 | 13351 | 9847 | 3504 | 0.096950916 |
| 6 | 13442 | 9683 | 3759 | 0.104006419 |
| 7 | 13498 | 10026 | 3472 | 0.096065519 |
| 8 | 13656 | 10508 | 3148 | 0.08710088 |
| 9 | 15412 | 12606 | 2806 | 0.077638205 |
| 10 | 14710 | 12272 | 2438 | 0.067456145 |
| 11 | 12932 | 10827 | 2105 | 0.058242488 |
| 12 | 12451 | 10465 | 1986 | 0.05494992 |
| 13 | 12289 | 10487 | 1802 | 0.04985889 |
| 14 | 12442 | 10872 | 1570 | 0.043439765 |
| 15 | 12443 | 11082 | 1361 | 0.03765702 |
| 16 | 11679 | 10650 | 1029 | 0.028471031 |
| 17 | 10671 | 9849 | 822 | 0.022743622 |
| 18 | 10104 | 9406 | 698 | 0.019312711 |
| 19 | 9044 | 8597 | 447 | 0.012367882 |
| 20 | 7830 | 7639 | 191 | 0.00528471 |

The above-described procedure was repeated for each of the other G, C, and T standard mixtures. The value of the resulting calibration matrix K is given below.

K =

| | | | |
|---|---|---|---|
| 0.06997656 | 0.00560156 | 0.0006317 | 0.00106842 |
| 0.12375633 | 0.01742844 | 0.00135174 | −0.000216 |
| 0.13982928 | 0.04116091 | 0.00123986 | 0.0001631 |
| 0.12371946 | 0.07320856 | 0.00467437 | 5.78E-05 |
| 0.09886611 | 0.09564174 | 0.01468073 | 0.00110168 |
| 0.07713955 | 0.10223842 | 0.03331307 | 0.00135638 |
| 0.06114513 | 0.09631226 | 0.06274018 | 0.00233467 |
| 0.05158994 | 0.08743771 | 0.09389819 | 0.00552211 |
| 0.04562928 | 0.07895128 | 0.11459118 | 0.01693018 |
| 0.03976041 | 0.06822545 | 0.11740752 | 0.04309424 |
| 0.03399378 | 0.06118095 | 0.1077492 | 0.08495856 |
| 0.02968821 | 0.05432655 | 0.09114524 | 0.12773016 |
| 0.0260446 | 0.04939954 | 0.0760703 | 0.15276644 |
| 0.02068053 | 0.04293259 | 0.06362222 | 0.14843742 |
| 0.01719018 | 0.03699554 | 0.05479123 | 0.12737328 |
| 0.0138741 | 0.03001199 | 0.05043105 | 0.10408945 |
| 0.0108418 | 0.02420318 | 0.04193956 | 0.07498112 |
| 0.00823091 | 0.01703111 | 0.03416537 | 0.05370087 |
| 0.00570478 | 0.01182548 | 0.0237908 | 0.03455896 |
| 0.00233907 | 0.00588673 | 0.01176649 | 0.01999116 |

EXAMPLE 2

Multicomponent Analysis of a Single Data Vector

The following example describes the application of the multicomponent analysis method of the invention to the analysis of data resulting from a 4-color DNA sequencing experiment. This example employs the calibration matrix derived in Example 1 above. The example will apply the multicomponent analysis method of the invention to a single data vector d collected during a DNA sequencing run.

The four color dye-labeled terminator reaction was prepared using the Applied Biosystems Dye Terminator Cycle Sequencing Ready Reaction Kit according to enclosed instructions (PE p/n 402079). The template was p-GEM® plasmid DNA and the forward 10 primer extension reaction was primed with −21M13 primer. Subsequent to the primer extension step, the reaction was ethanol precipitated and the dried product taken up in 25 μl of Template Suppression Reagent and denatured by heating at 95° C. for 2 minutes. The electrophoresis was performed as described above.

Data vector d collected at scan 1685 is shown below. The data shown in the table have been subjected to baseline correction and normalization to unit area. Baseline correction for each channel was accomplished by (i) scanning the entire run for the minimum value for that channel and (ii) subtracting that minimum value from the corresponding element in data vector d.

| d= |
|---|
| 0.0030 |
| 0.0057 |
| 0.0090 |
| 0.0143 |
| 0.0231 |
| 0.0391 |
| 0.0617 |
| 0.0873 |
| 0.1048 |
| 0.1089 |
| 0.1020 |
| 0.0881 |
| 0.0752 |
| 0.0638 |
| 0.0556 |
| 0.0494 |
| 0.0407 |
| 0.0323 |
| 0.0228 |
| 0.0131 |

The concentration estimate vector c was computed using the classical multiple regression method, where, $$c = (K^T K)^{-1} K^T d$$

where the values of K and d have been provided above. The value of c is given below.

| c= |
|---|
| 0.0320 |
| 0.0768 |
| 0.8480 |
| 0.0427 |

Next, the residual vector r of the concentration estimate vector c was determined, where $$r = d - Kc$$

where values for d, K, and c are provided above. The value of residual vector r is provided below.

| r= |
|---|
| −0.0002 |
| −0.0008 |
| 0.0003 |
| 0.0007 |
| 0.0001 |
| 0.0005 |

-continued r=

```
-0.0009
-0.0009
-0.0006
 0.0010
 0.0012
 0.0002
-0.0004
-0.0005
 0.0004
-0.0006
-0.0003
-0.0005
 0.0000
 0.0017
```

Next, the variance of the data vector, var(d), was calculated, where $$\text{var}(d) = \frac{r^T r}{(n_c - n_p)}$$

The value of var(d) was found to be $6.3270 * 10^{-7}$.

The variance-covariance matrix of the concentration estimate vector varcovar(c) was then evaluated according to the relation $$\text{varcovar}(c) = \text{var}(d) \, (K^T K)^{-1}.$$

The value of the variance-covariance matrix varcovar(c) is shown below.

varcovar(c)*10$^4$=

| 0.2441 | -0.3311 | 0.1533 | -0.0162 |
|---|---|---|---|
| -0.3311 | 0.7301 | -0.4594 | 0.0695 |
| 0.1533 | -0.4594 | 0.4905 | -0.1588 |
| -0.0162 | 0.0695 | -0.1588 | 0.1340 |

Finally, the confidence intervals $CI_i$ for each element of the concentration estimate vector was determined where, $$CI_i = c_i \pm (\text{varcovar}(c_{ii}))^{1/2} Q_{(cl, nf)}$$

In this example, the Student's t-distribution was used as the statistical distribution The value of Q was determined by reference to tabulated values based on 16 ($n_c - n_p$) degrees of freedom, and a 99% confidence level. The resulting value for Q was 2.92. The values of the plus and minus confidence intervals for each $c_i$ are provided below.

```
CI₁ = 0.0320 ± 0.0144
CI₂ = 0.0768 ± 0.0250
CI₃ = 0.8480 ± 0.0204
CI₄ = 0.0427 ± 0.0107
```

EXAMPLE 3

Improved Base-Calling Using the Multicomponent Analysis Method of the Invention

The following example describes the application of the multicomponent analysis method of the invention to the analysis of multiple data vectors (one data vector for each scan number) resulting from a 4-color DNA sequencing experiment. This example will employ the calibration matrix derived in Example 1 above.

Figure 5A:
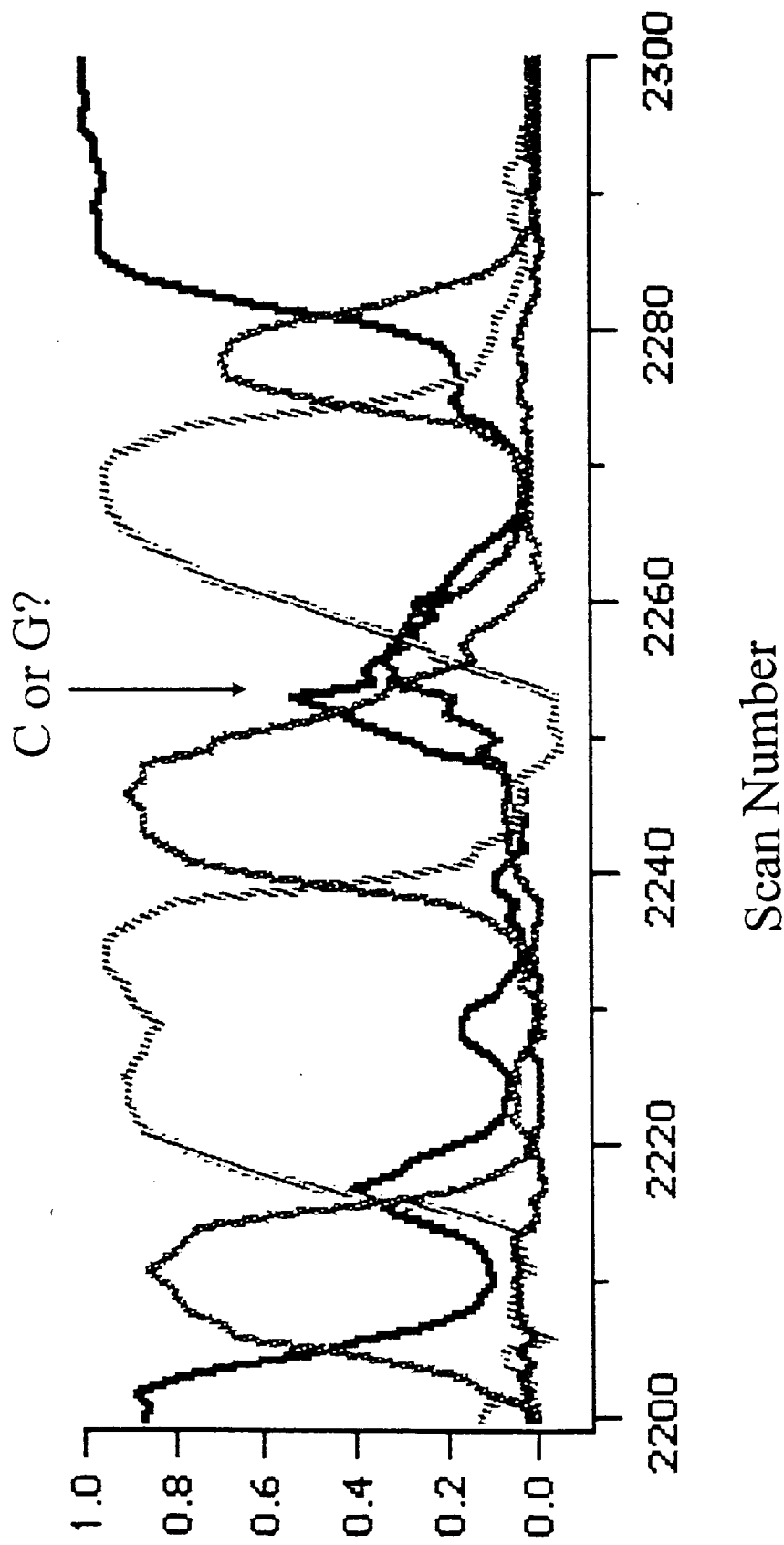
FIGS. 5a and 5b compare the results of a DNA sequencing experiment using conventional multicomponent analysis methods (5a) and the improved multicomponent analysis methods of the invention (5b).

FIG. 5a shows a portion of an electropherogram collected as part of a DNA sequencing experiment showing the known sequence TAATCATGG. The sequencing template was pGEM® plasmid DNA and the experimental conditions were as described above. FIG. 5a was obtained using conventional data analysis methods wherein four detector channels were used, at 535, 555, 575, and 605 nm respectively, with a bandwidth of 7 nm for each channel. The important feature of FIG. 5a is that interference from the G signal makes the base assignment of the C base at approximate scan number 2255 ambiguous. Because the 4-channel system is an exactly determined system, no confidence interval can be estimated to compare the likelihood of the base being a C or G.

Figure 5B:
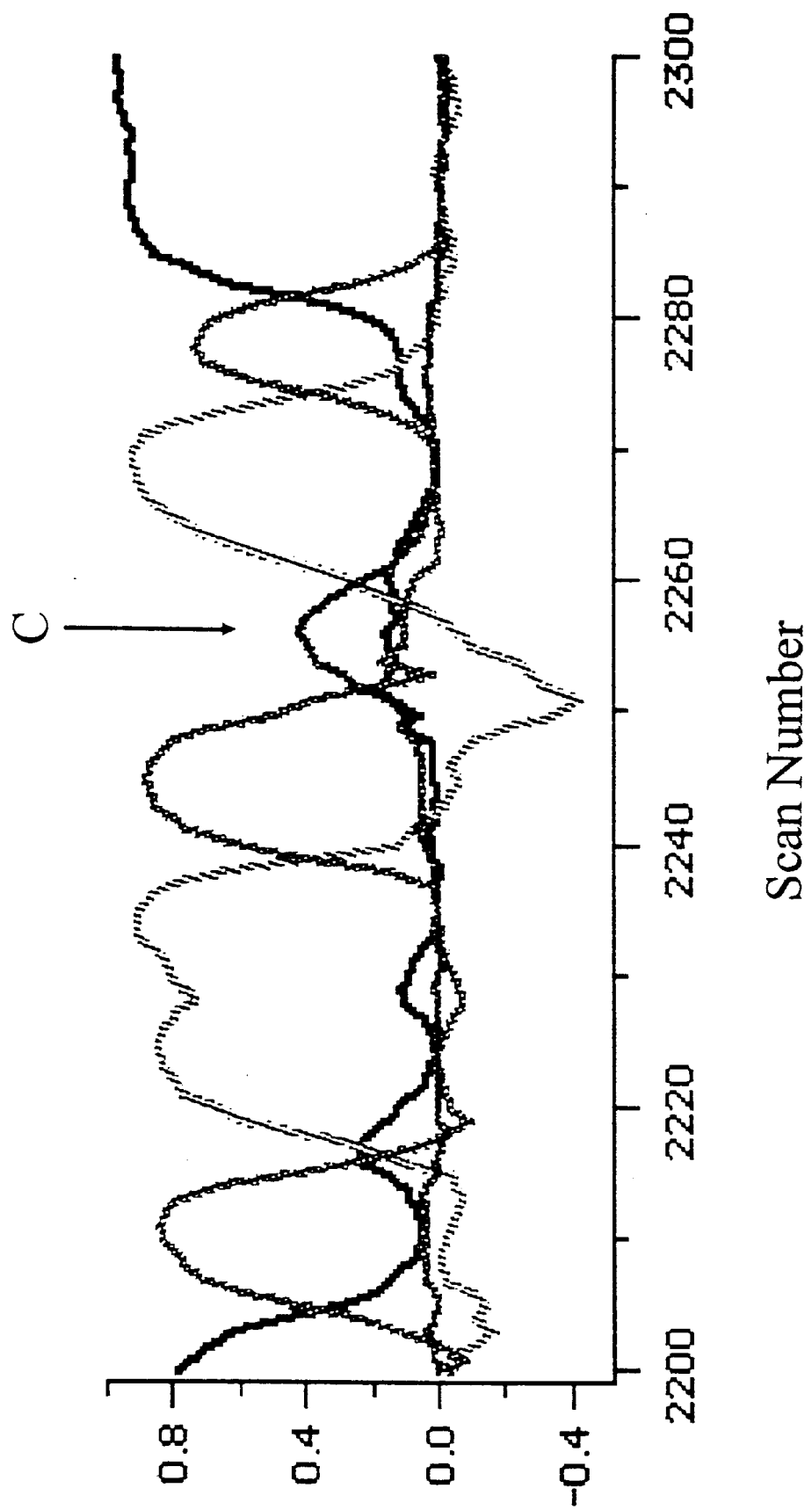

FIG. 5b shows the same electropherogram as FIG. 5a, with the difference that the data were analyzed using the overdetermined multicomponent analysis method of the present invention. In FIG. 5b, 20 channels were monitored rather than 4. The plot of FIG. 5b shows only the lower bound of the 99% confidence interval of the data based on a Student's t distribution with 16 degrees of freedom. As can be seen from the figure, by presenting only the 99% confidence values, the base whose identity was uncertain based on the data from FIG. 5a can be clearly identified as a C.

All publications and patent applications cited herein are hereby incorporated by reference to the same extent as if each individual publication or patent application was specifically and individually indicated to be incorporated by reference.

Although only a few embodiments have been described in detail above, those having ordinary skill in the art will clearly understand that many modifications are possible in the preferred embodiment without departing from the teachings thereof. All such modifications are intended to be encompassed within the following claims.

I claim:

1. A signal processing method in a processor for performing a multicomponent analysis of a signal resulting from a spectral response of a mixture comprising a plurality of spectrally resolvable molecular species, including the determination of a concentration estimate and a statistical confidence interval for each species, such method comprising the steps of:

receiving a data vector d from a multichannel detector, data vector d having length $n_c$, $n_c$ being the number of detector channels being monitored, the magnitude of each vector element $d_i$ representing a signal intensity at a particular channel i;

providing a calibration matrix K having $n_c$ rows and $n_p$ columns wherein $n_c$ is larger than $n_p$, $n_p$ being the number of spectrally resolvable molecular species, the magnitude of each matrix element $K_{ij}$ representing a calibration value at a particular channel i for a particular species j;

determining a concentration estimate vector c having length $n_p$, the magnitude of each vector element $c_i$ representing a concentration estimate of a particular species i;

determining a confidence interval $Ci_i$ for each of the elements of the concentration estimate vector according to the expression $$CI_i = c_i \pm (\text{varcovar}(c_{ii}))^{1/2} Q_{(cl, nf)}$$

where Q is a critical value of a statistical distribution for a given level of confidence, cl, and a given number of degrees of freedom $n_f$, where $n_f = n_c - n_p$.

2. The method of claim 1 wherein $n_c$ is greater than 10.
3. The method of claim 1 wherein $n_c$ is greater than 20.
4. The method claim 1 wherein $n_c/n_p$ is greater than 1.5.
5. The method claim 1 wherein $n_c/n_p$ is greater than 3.0.
6. The method claim 1 wherein $n_c/n_p$ is greater than 5.0.
7. The method claim 1 wherein the statistical distribution is the Student's t distribution.
8. The method claim 1 wherein the method is repeated at regular intervals for a defined period.
9. The method of claim 1 wherein the determining of a concentration estimate vector is effected using the expression $$c=(K^TK)^{-1}K^Td.$$

10. The method of claim 1 wherein the determining of a confidence interval comprises the steps of:

determining a residual vector r of the concentration estimate vector c where $$r=d-Kc$$

determining a variance of the data vector d, var(d), where $$\text{var}(d) = \frac{r^Tr}{(n_c - n_p)}$$

and, determining a variance-covariance matrix of the concentration estimate vector c, varcovar(c), where $$\text{varcovar}(c)=\text{var}(d)(K^TK)^{-1}$$

11. A program storage device readable by a machine, tangibly embodying a program of instructions executable by a machine to perform method steps to perform a multicomponent analysis of a signal resulting from a multichannel detector, including the determination of a statistical confidence interval, said method steps comprising:

receiving a data vector d from a multichannel detector, data vector d having length $n_c$, $n_c$ being the number of detector channels being monitored, the magnitude of each vector element $d_i$ representing a signal intensity at a particular channel i;

providing a calibration matrix K having $n_c$ rows and $n_p$ columns wherein $n_c$ is larger than $n_p$, $n_p$ being the number of spectrally resolvable molecular species, the magnitude of each matrix element $K_{ij}$ representing a calibration value at a particular channel i for a particular species j;

determining a concentration estimate vector c having length $n_p$, the magnitude of each vector element $c_i$ representing a concentration estimate of a particular species i;

determining a confidence interval $CI_i$ for each of the elements of the concentration estimate vector according to the expression $$CI_i=c_i\pm(\text{varcovar}(c_{ii}))^{1/2}Q_{(cl,nf)}$$

where Q is a critical value of a statistical distribution for a given level of confidence, cl, and a given number of degrees of freedom $n_f$, where $n_f=n_c-n_p$.

12. A method of polynucleotide sequencing comprising the steps of:

(a) forming a mixture of a first, a second, a third, and a forth class of labeled polynucleotides such that each polynucleotide in the first class includes a 3'-terminal dideoxyadenosine and is labeled with a first label, each polynucleotide in the second class includes a 3'-terminal dideoxycytidine and is labeled with a second label, each polynucleotide in the third class includes a 3'-terminal dideoxyguanosine and is labeled with a third label, and each polynucleotide in the forth class includes a 3'-terminal dideoxythymidine and is labeled with a forth label, wherein each of the first, second, third, and fourth labels are spectrally resolved;

(b) electrophoretically separating the labeled polynucleotides thereby forming multiple bands of similarly sized polynucleotides;

(c) detecting the bands using a spectral array detector having $n_c$ channels, where $n_c$ is greater than four, (d) providing a calibration matrix K having $n_c$ rows and $n_p$ columns wherein $n_c$ is larger than $n_p$, $n_p$ being the number of spectrally resolvable molecular species, the magnitude of each matrix element $K_{ij}$ representing a calibration value at a particular channel i for a particular species j;

(e) determining a concentration estimate vector c having length $n_p$, the magnitude of each vector element $c_i$ representing a concentration estimate of a particular species i;

(f) determining a confidence interval $CI_i$ for each of the elements of the concentration estimate vector according to the expression $$CI_i=c_i\pm(\text{varcovar}(c_{ii}))^{1/2}Q_{(cl,nf)}$$

where Q is a critical value of a statistical distribution for a given level of confidence, cl, and a given number of degrees of freedom $n_f$, where $n_f=n_c-n_p$;

(g) reporting values of $c_i$ and $CI_i$; and (i) repeating steps (c)–(g) until all bands of interest have been analyzed.

13. An apparatus for measuring the spectral response of a sample including a mixture containing $n_p$ spectrally distinguishable species comprising:

a spectral array detector for detecting the spectral response of the sample, the detector having $n_c$ channels where $n_c$ is greater than $n_p$, the output of the detector being a signal representing a light intensity at a particular channel at a particular time;

a signal processor for receiving a signal from the spectral array detector, the signal processor being configured to perform the following steps:

receiving a data vector d from the spectral array detector, data vector d having length $n_c$, $n_c$ being the number of detector channels being monitored, the magnitude of each matrix element $d_i$ representing a signal intensity at a particular channel i;

providing a calibration matrix K having $n_c$ rows and $n_p$ columns wherein $n_c$ is larger than $n_p$, $n_p$ being the number of spectrally resolvable molecular species, the magnitude of each matrix element $K_{ij}$ representing a calibration value at a particular channel i for a particular species j;

determining a concentration estimate vector c having length $n_p$, the magnitude of each matrix element $c_i$ representing a concentration estimate of a particular species i;

determining a confidence interval for each of the elements of the concentration estimate vector $CI_i$ according to the expression $$CI_i = c_i \pm (\text{varcovar}(c_{ii}))^{1/2} Q_{(cl, nf)}$$

where Q is the critical value of a statistical distribution for a given level of confidence, cl, and a given number of degrees of freedom $n_f$ where $n_f = n_c - n_p$.

* * * * *

UNITED STATES PATENT AND TRADEMARK OFFICE
CERTIFICATE OF CORRECTION

PATENT NO. : 6,015,667
DATED : January 18, 2000
INVENTOR(S) : Muhammad A. Sharaf It is certified that error appears in the above-identified patent and that said Letters Patent is hereby corrected as shown below:

On the title page: Item [73] Assignee:

"The Perkin-Emer Corporation" should read --The Perkin-Elmer Corporation--.

Signed and Sealed this

Seventeenth Day of October, 2000

Attest:

Q. TODD DICKINSON

*Attesting Officer*     *Director of Patents and Trademarks*